United States Patent

Huynh-Ba et al.

[11] Patent Number: 5,747,302
[45] Date of Patent: May 5, 1998

[54] PREPARATION OF THIOLS WITH FOOD-ACCEPTABLE MICRO-ORGANISMS

[75] Inventors: Tuong Huynh-Ba, Pully; Daniel Jaeger, St-Cierges; Walter Matthey-Doret, Belmont S/Lausanne, all of Switzerland

[73] Assignee: Nestec S.A., Vevey, Switzerland

[21] Appl. No.: 736,261

[22] Filed: Oct. 24, 1996

[30] Foreign Application Priority Data

Oct. 25, 1995 [EP] European Pat. Off. ............ 95202889

[51] Int. Cl.$^6$ .................. C12P 17/00; C12P 11/00; C12N 1/16
[52] U.S. Cl. .................. 435/117; 435/130; 435/171; 435/232; 435/942
[58] Field of Search .................. 435/232, 117, 435/130, 171, 942

[56] References Cited

U.S. PATENT DOCUMENTS 4,031,256  6/1977  Evers et al. .................. 426/535
4,041,186  8/1977  Evers et al. .................. 426/535
5,182,194  1/1993  Kerkenaar et al. .................. 435/130

OTHER PUBLICATIONS

Chem. Abs. 116:101505n (1992) Ohmori et al. Abstract of J. Chromatog 1992 574(1) 35–40.

van der Schaft et al., "Microbial Production of Natural Furfurylthiol", Trends in Flavor Research, 35, 437–438, 1994, Elsevier Science B.V.

Tateishi, et al., "Cysteine Conjugate β–Lyase in Rat Liver", J. Biol. Chem. 253(24), pp. 8854–8859, 1978.

*Primary Examiner*—Herbert J. Lilling
*Attorney, Agent, or Firm*—Vogt & O'Donnell, LLP

[57] ABSTRACT

Flavorant compounds and compositions for food substances are prepared in a food-acceptable manner by bio-conversion of a cysteine S-complex with a food-acceptable micro-organism, particularly a yeast or filamentous fungus, which, upon incubation with the complex, splits the complex at a terminal carboxyl group in a beta position to yield a product including a thiol and at least one metabolite compound, and the product is isolated.

22 Claims, No Drawings

PREPARATION OF THIOLS WITH FOOD-ACCEPTABLE MICRO-ORGANISMS

The invention relates to the preparation of thiols, in particular natural flavouring thiols, by bioconversion.

Thiols are among the volatile sulphur-containing substances which are considered to be responsible for the meaty note of various meats, for example, chicken, beef and pork, or which are components of the flavour of coffee.

Meat flavourings are generally produced by a thermal reaction between a reducing sugar and an amino acid in the presence of a sulphur-containing compound as the source of sulphur, for example cysteine, at a high temperature for a certain period of time, optionally in the presence of fat. Such a reaction provides a complex mixture of aromatic substances entering into the composition of the flavour of meat. It is known, for example from U.S. Pat. No. 5,182,194, that certain micro-organisms which cannot be used in food are able to provide a beta-C-S-lyase enzyme capable of producing thiols from cysteine S-complexes.

SUMMARY OF THE INVENTION

The object of the invention is to provide natural thiols which are obtained by bio-conversion and which are capable of being used as a flavoring ingredient for foods.

The process according to the invention is characterized in that a cysteine S-complex with the formula:

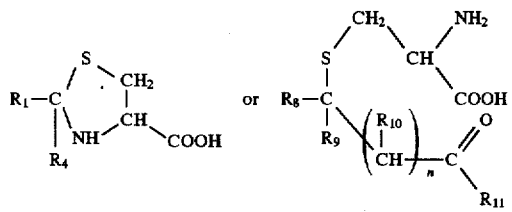

in which:

$R_1$ is H, $C_{1-7}$ linear or branched alkyl, phenyl, benzyl, 2-$R_2$-2-$R_3$-vinyl, 5-$R_2$-furan-2-yl, 5-$R_2$-thiofuran-2-yl, $R_2$ and $R_3$ are similar or different and represent H or $CH_3$, $R_4$ is H, or forms with $R_1$ a 2-$R_5$-5-$R_6$-tetrahydrofuran-3-ylidene, or 2-$R_5$-5-$R_6$-2,3-dihydrofuran-3-ylidene group, in which $R_5$ and $R_6$ are similar or different and represent H or $CH_3$, or $R_4$ is a $CH(OH)R_7$ group and $R_7$ represents H, $C_{1-4}$-alkyl or phenyl, $R_8$, $R_9$ and $R_{10}$ are similar or different and represent H or $C_{1-4}$-alkyl, $R_{11}$ represents H, $C_{1-4}$-alkyl, phenyl, $C_{1-4}$-alkoxy, or $C_{1-4}$alkylamino and n is 0 or 1, is put into contact with a micro-organism which can be used in food, having an enzymatic activity of the beta-C-S-lyase type.

Within the context of the invention, an $R_1$ radical with $C_{1-7}$ is preferably methyl, ethyl, n-propyl, isopropyl, n-butyl, isobutyl, sec-butyl, n-hexyl or n-heptyl.

An $R_8$ to $R_{10}$ radical is preferably H or methyl and $R_{11}$ is preferably methyl, ethyl, phenyl, methoxy, ethoxy, methylamino or ethylamino.

Included in the present invention are products of the preceding reaction which comprise thiols and metabolites and the use of the products in a food, as they are, in a flavouring composition, or as a flavour enhancer, and thus, the flavorant products may be incorporated in foods intended for human or animal consumption.

DETAILED DESCRIPTION OF THE INVENTION

In practice of the present invention, under the action of beta-C-S-lyase, the cysteyl radical of the complex compound is split in the beta position from the end carboxyl group leading to the corresponding thiol.

When n is 0, the compound formed by the action of beta-C-S-lyase is then an alpha-mercapto aldehyde, an alpha-mercaptoacetone, an alpha-mercaptoester or an alpha-mercaptoamide.

When n=1, the compound formed by the action of beta-C-S-lyase is then a beta-mercapto aldehyde, a beta-mercaptoacetone, a beta-mercaptoester or a beta-mercaptoamide.

The preferred compounds liberated by beta-C-S-lyase are furfuryl thiol (FFT), benzyl thiol, 5-methylfurfuryl thiol, 2-methylfuran-3-thiol, 2,5-dimethylfuran-3-thiol, 2-methyltetrahydrofuran-3-thiol and 3-methyl-2-butene-1-thiol.

These compounds contribute significantly to the generation of flavours of the meat, chicken, beef and pork type, and also of coffee as regards furanthiols and 3-methyl-2-butene-1-thiol.

It has been found that the preceding preferred compounds can be partly metabolized into furfuryl methyl sulphide (Me-FFT), S-furfurylthio acetate (Ac-FFT) and bis-furfuryl disulphide (Di-FFT). These metabolites also possess a characteristic meaty note and may also contribute to the formation of flavour.

According to the invention, the micro-organisms involved are those which can be used in food and are capable of possessing enzymatic activity of the beta-C-S-lyase type. In the present specification, a micro-organism which can be used in foods means any food-quality, or food-acceptable, micro-organism, whether this be for human or animal consumption.

These are preferably yeasts and filamentous fungi or moulds. Among the yeasts, reference may particularly be made to baker's yeast, Saccharomyces cerevisae, but also, for example, brewer's yeast, and the yeasts Candida versatilis, Debaromyces hansenii, Saccharomyces bayanus and Saccharomyces rouxii. Among the filamentous fungi, reference may be made, for example, to Aspergillus oryzae, Penicillium roqueforti and Penicillium camemberti.

Cysteine complexes able to act as a substrate in bioconversion according to the invention may be easily obtained by reacting an aldehyde or a ketone of the formula $R_1$—CHO or $R_1.R_4$—CO or a ketone, ester or amide, alpha, beta-unsaturates of the formula $CR_8.R_9$=$(CR_{10})_nCOR_{11}$, in which $R_1$ to $R_{11}$ have the preceding meanings, with cysteine in a water-alcohol medium at room temperature.

The incubation reaction with a micro-organism takes place under conditions for activating the C-S-lyase enzyme of the micro-organism. This may be under anaerobic or aerobic conditions, preferably anaerobic, for 5 to 72 hours and preferably for 12 to 48 hours at pH 6–9, preferably at pH 7–8, with medium to strong stirring and at a temperature of 20° to 50° C. and preferably around 30° C. The concentration of the substrate, namely of the complex in the culture medium is from 1 to 100 mmol and preferably 20 to 40 mmol.

In particular, in the case of baker's yeast, it is preferred to operate under anaerobic conditions, for example under an inert gas such as nitrogen, so as to minimize the generation of metabolites of the baker's yeast itself and conversion products of such metabolites, for example by oxidation, and hence to direct fermentation to the production of thiols.

Baker's yeast may be used in the form of a cream or extract. It is preferably fresh, in particular 0 to 18 days old, and advantageously 0 to 8 days old, kept in a refrigerator.

Incubation may be carried out by adding the substrate in one or more steps, preferably progressively, taking into account the kinetics of the enzymatic reaction, so that the latter does not inhibit the activity of the enzyme. With the same idea in mind, it could be possible to consider increasing the quantity of substrate and to isolate the volatile thiols as they are produced, so as to increase the yield and rate of the lysis reaction. For this purpose, volatile organic compounds can be attached to a support, for example a resin, and then eluted. They can also be extracted during incubation in a two-phase medium with the aid of a water-immiscible solvent, preferably of food quality, for example pentane or hexane.

Following incubation, the thiols may be extracted with a solvent, preferably of food quality, for example pentane or hexane, and can be purified by conventional methods known to a person skilled in the art.

As a variant, the thiols formed in the supernatant can be isolated, for example by centrifuging, and then optionally concentrated and dried, for example by spraying or lyophilizing in the presence of a solid support, for example maltodextrin. Drying takes place under moderate conditions, for example at a temperature of <70° C. under vacuum.

The invention also concerns the use of a product of the preceding reaction containing thiols and their metabolites in a food, as it is, in a flavouring composition or as a flavour enhancer.

Such flavours may be incorporated in foods intended for human or animal consumption. In the present specification a micro-organism which can be used in foods is understood to mean any food quality micro-organism, whether this be for human or animal consumption.

EXAMPLES

The following examples illustrate the invention. In these examples, percentages and parts are by weight unless indicated to the contrary.

Examples 1 to 4
Preparation of cream of baker's yeast

Commercial cream of baker's yeast, *Saccharomyces cerevisae*, containing 22–28% dry matter, was clarified by centrifuging and the supernatant was discarded. The sediment was then mixed with a 0.1M aqueous solution of phosphate buffer at pH 7.5.

Preparation of a cysteine-furfural complex or 2-(2-furyl)-1,3-thiazolidine-4-carboxylic acid 7.7 g (63.6 mmol) of cysteine were dissolved in 200 ml of a 40% aqueous solution of ethanol in a reactor. A solution of 7 g (72.9 mmol) of furfural in 20 ml of ethanol was then added drop-wise with stirring. The light yellow solution was left stirring and the appearance of a precipitate was observed at the end of 1 hour. After having placed the reactor in an ice bath for 1 hour, the precipitate was separated by filtration, washed with 2×50 ml of ethanol and dried under reduced pressure. 10.95 g of a whitish powder of cysteine-furfural complex were thus obtained with a yield of 86.5%.

The structure of the compound, verified by electron impact mass spectrography (MS/EI) and by nuclear magnetic resonance of the proton in dimethyl sulphoxide ($^1$H-NMR) showed the presence of two cis/trans diastereoisomers in a ratio of 1:2.

Incubation 100 ml of the preceding cream of whole baker's yeast cells were then placed in a reactor fitted with a pH electrode, a condenser and a magnetic stirrer revolving at 600 rpm. The reactor was placed in an oil bath thermostatically controlled at 30° C. The reactor was linked to a pH-stat keeping the pH at the chosen value (6.9 or 8) by addition of a 2N aqueous solution of sodium hydroxide. In the case of an anaerobic test, nitrogen was bubbled through the suspension for 15 min by means of a tube in the outlet from the condenser and the reactor was kept under nitrogen for the period of incubation. 0.4 g (2 mmol) and 0.8 g (4 mmol) respectively of 2-(2-furyl)-1,3-thiazolidine-4-carboxylic acid were added to this and 5 ml samples were taken at various incubation times.

Analysis of bioconversion results

After having adjusted the pH of the sample to 4 with a 2N aqueous solution of hydrochloric acid, 500 microlitres of a solution of benzyl thiol in pentane (2000 ppm) were added as an internal standard. After adding 3 g of sodium chloride, the sample was extracted with 3×15 ml of diethyl ether, the extracts were separated from the reaction medium by centrifuging (15 min., 5000 rpm), and these were combined, dried over sodium sulphate and concentrated in a Vigreux column to a volume of 2 ml, and the concentrated solution obtained was placed in a freezer at –20° C. until analysed.

Analysis by gas chromatography was carried out on a Carlo Erba Mega 2 chromatograph fitted with a cold injector and a flame ionization detector (GC-FID). A flame photometric detector (GC-FPD) was used for the sulphur compounds. The capillary columns were DB-5, DB-1701, DB-Wax and DB-FFAP, 30 m×0.32 mm, film thickness 0.25 micron, from J & W Scientific, Folsom, USA. The carrier gas was helium (65 kPa) with an addition of nitrogen (40 kPa) for the GC-FID. The retention indices (RI) were calculated by linear interpolation.

The analyses were confirmed by establishing spectra produced by coupling a gas chromatograph with an electron impact mass spectrograph (GC/EI-MS, HP 5890/HP 5971) under the same operating conditions as for GC-FID.

The results for the principal sulphur compounds relating to aerobic incubation are shown below in table 1 and those concerning anaerobic incubation in table 2.

TABLE 1

| Compound | RI (DB-Wax), FID | RI (DB-Wax), FPD | RI (FFAP), FPD | RI (DB5), FPD | RI (DB-1701), FPD |
|---|---|---|---|---|---|
| S-methyl thioacetate | 1037 | 1039 | 1048 | — | — |
| S-ethyl thioacetate | 1087 | 1088 | 1090 | — | — |
| Thioacetic acid | — | 1148 | — | — | 713 |
| Diethyl disulphide | 1208 | 1192 | — | — | — |
| 2-thio-1-ethanol | — | 1502 | 1500 | — | — |
| S-furfuryl-thio thioacetate | 2215 | 2217 | — | — | — |
| FFT | 1434 | 1438 | 1437 | 908 | 1000 |
| Me-FFT | 1486 | 1487 | 1487 | 998 | 1091 |
| Ac-FFT | 1768 | 1769 | 1770 | 1159 | 1276 |
| Di-FFT | 2570 | 2570 | 2602 | 1690 | 1864 |

TABLE 2

| Compound | RI (DB-Wax), FID | RI (DB-Wax), FPD | RI (FFAP), FPD | RI (DB5), FPD | RI (DB-1701), FPD |
|---|---|---|---|---|---|
| FFT | 1435 | 1440 | 1438 | 911 | 1000 |
| Me-FFT | 1487 | 1487 | 1487 | 998 | 1091 |
| Ac-FFT | 1768 | 1768 | 1769 | 1159 | 1276 |
| Di-FFT | — | 2570 | 2600 | 1689 | 1864 |

—: not determined

It was noted that aerobic incubation produced other sulphur compounds in addition to those sought (FFT, Me-FFT, Ac-FFT and Di-FFT). These other compounds probably resulted from the metabolism of cysteine.

Anaerobic incubation mainly produced the compounds sought.

Table 3 below gives the yield of FFT, calculated as a % of the starting complex, as a function of the incubation conditions. In examples 1–4, the yeast used was 4 days old.

TABLE 3

| Example | 1 | 2 | 3 | 4 |
|---|---|---|---|---|
| Aerobic | + | − | − | − |
| Anaerobic | − | + | + | + |
| pH | 6.9 | 6.9 | 6.9 | 8 |
| Concentration of substrate (mmol) | 20 | 20 | 40 | 20 |
| Yield of FFT (%) after (days) | | | | |
| 1 | 25.4 | 14 | 2.2 | 36.9 |
| 2 | 15 | 27.8 | 5 | 27.5 |
| 3 | 11 | 26 | 6 | 16 |
| 4 | 6 | 24 | 5 | 12 |
| 7 | 2 | 8 | 6 | 8 |

Example 5

Incubation was carried out under the same conditions as for example 2, except for the 8 day yeast. Table 4 below gives the total yield of FFT and its metabolites as well as individual yields.

TABLE 4

| Yield (%) | After 1 day | After 2 days | After 3 days | After 4 days | After 7 days |
|---|---|---|---|---|---|
| Total | 8.1 | 16.5 | 17.4 | 18.1 | 16.6 |
| FFT | 6.2 | 15 | 14 | 12.5 | 13.2 |
| Me-FFT | — | 0.5 | 0.5 | 1 | 0.5 |
| Ac-FFT | 1.9 | 1 | 1.9 | 2.6 | 0.5 |
| Di-FFT | — | — | 1 | 2 | 2.4 |

—: not determined

Example 6

Incubation was carried out under the same conditions as for example 4, except for the 8 day yeast. Table 5 below gives the total yield of FFT and its metabolites as well as individual yields.

TABLE 5

| Yield (%) | After 1 day | After 2 days | After 3 days | After 4 days | After 7 days |
|---|---|---|---|---|---|
| Total | 41 | 32 | 22 | 17 | 24 |
| FFT | 37 | 28 | 17 | 13 | 8 |
| Ac-FFT | 2 | — | — | — | — |
| Di-EFT | 2 | 4 | 5 | 4 | 16 |

—: not determined

Example 7

Incubation was carried out under the same conditions as for example 2, except that fresh yeast (0 days) and 18 day yeast were used respectively. In order to carry out incubation with an 18 day yeast, the yeast was kept in a refrigerator at 4° C. Just before use, the phosphate buffer solution was removed by centrifuging and was replaced by the same volume of fresh buffer.

Table 6 below gives the yield of FFT.

TABLE 6

| FFT Yield (%) | After 1 day | After 2 days | After 3 days | After 4 days | After 7 days |
|---|---|---|---|---|---|
| Fresh yeast | 1 | 16 | 24 | — | — |
| 18 day yeast | 13 | 22 | 22.5 | 20 | 9 |

—: not determined

Examples 8 to 10

Proceeding as in example 2, the following complexes were incubated:

8. Cysteine-benzaldehyde and its bioconversion into benzyl thiol was obtained.

9. 5-methyl-furfuryl-cysteine and its bioconversion into 5-methyl-furfuryl thiol was obtained, and 10. 2-methyl-tetrahydrofuranyl-cysteine, which led to 2-methyl-tetrahydrofuran-3-thiol.

Examples 11 to 13

Proceeding in a similar manner to that used in example 2, conversion of cysteine-furfural into FFT was obtained by incubation with the following micro-organisms:

11. *Candida versatilis*

12. *Debaromyces hansenii*

13. *Saccharomyces bayanus*.

We claim:

1. A process for food-acceptable preparation of flavorant compounds comprising:

obtaining a cysteine S-complex having a formula selected from the group consisting of

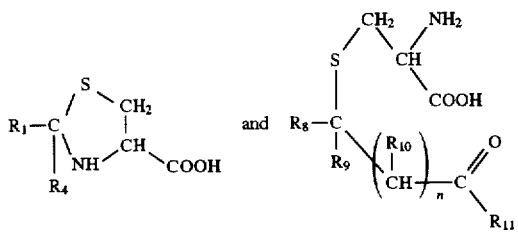

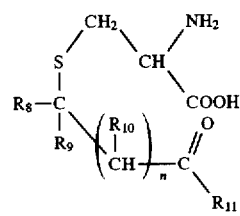

wherein

- $R_1$ is selected from the group consisting of H, $C_{1-7}$ alkyls, phenyl, benzyl, 2-$R_2$-2-$R_3$-vinyl, 5-$R_2$-furan-2-yl and 5-$R_2$-thiofuran-2-yl wherein $R_2$ and $R_3$ are selected from the group consisting of H and $CH_3$, and
- $R_4$ is selected from the group consisting of H and CH(OH) $R_7$, wherein $R_7$ is selected from the group consisting of H, $C_{1-4}$ alkyls and phenyl, or
- $R_1$ and $R_4$, in combination, comprise a structure selected from the group consisting of 2-$R_5$-5-$R_6$-tetrahydrofuran-3-ylidene and 2-$R_5$-5-$R_6$-2,3-dihydrofuran-3-ylidene wherein $R_5$ and $R_6$ are selected from the group consisting of H and $CH_3$,
- $R_8$, $R_9$ and $R_{10}$ are selected from the group consisting of H and $C_{1-4}$ alkyls,
- $R_{11}$ is selected from the group consisting of H, $C_{1-4}$ alkyls, phenyl, $C_{1-4}$ alkoxys and $C_{1-4}$ alkylaminos, and
- n is selected from the group consisting of 0 and 1;

combining the complex with a medium comprising a yeast microorganisms which are food-acceptable and selected from the group consisting of *Saccharomyces cerevisiae*, brewer's yeast, *Candida versatilis*, *Debaromyces hansenii*, *Saccharomyces bayanus* and *Saccharomyces rouxii* to obtain a complex-containing medium and incubating the complex-containing medium to split the complex to yield a product-containing reaction medium comprising compounds comprising a thiol and at least one metabolite compound; and isolating a product from the product-containing reaction medium which comprises the compounds to obtain a flavorant product.

2. A process according to claim 1 wherein the food-acceptable microorganism is *Saccharomyces cerevisiae*.

3. A process according to claim 1 wherein the complex has the formula

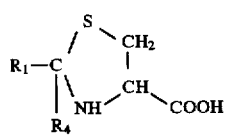

4. A process according to claim 3 wherein the food-acceptable microorganism is *Saccharomyces cerevisiae*.

5. A process according to claim 3 or 4 wherein the complex comprises the $R_1$ and $R_4$ structure-combination.

6. A process according to claim 3 or 4 wherein $R_1$ is selected from the group consisting of methyl, ethyl, n-propyl, isopropyl, n-butyl, iso-butyl, sec-butyl, n-hexyl and n-heptyl.

7. A process according to claim 1 wherein the complex has the formula

8. A process according to claim 7 wherein the food-acceptable microorganism is *Saccharomyces cerevisiae*.

9. A process according to claim 7 or 8 wherein $R_8$, $R_9$ and $R_{10}$ are selected from the group consisting of H and methyl and wherein $R_{11}$ is selected from the group consisting of methyl, ethyl, phenyl, methoxy, ethoxy, methylamino and ethylamino.

10. A process according to claim 1 or 2 wherein the yeast is up to 18 days old.

11. A process according to claim 1 or 2 wherein the yeast is a cream yeast.

12. A process according to claim 1 or 2 wherein the complex-containing medium contains the complex in an amount of from 1 mmol to 100 mmol and is incubated under anaerobic conditions at a temperature of from 20° C. to 50° C. for from 5 hours to 72 hours at a pH of from 6 to 9 with stirring.

13. A process according to claim 12 wherein the complex-containing medium contains the complex in an amount of from 1 mmol to 100 mmol and amounts of the complex are added to the complex-containing medium progressively during the incubation.

14. A process according to claim 1 or 2 wherein the complex-containing medium contains the complex in an amount of from 1 mmol to 100 mmol and amounts of the complex are added to the complex-containing medium during incubation.

15. A process according to claim 1 or 2 wherein the compounds are isolated during incubation.

16. A process according to claim 1 or 2 wherein the compounds are isolated on a support during incubation.

17. A process according to claim 1 or 2 wherein a food-acceptable water-immiscible solvent is present with the product-containing reaction medium for forming a two-phase medium for isolating the compounds from the product-containing reaction medium during incubation.

18. A process according to claim 1 or 2 wherein the compounds are isolated by obtaining a supernatant from the product-containing reaction medium and drying the supernatant with a support.

19. A process for food-acceptable preparation of thiol compounds comprising obtaining a cysteine S-complex and combining the complex with a medium comprising yeast microorganisms which are food-acceptable and selected from the group consisting of *Saccharomyces cerevisiae*, brewer's yeast, *Candida versatilis*, *Debaromyces hansenii*, *Saccharomyces rouxii* to obtain a complex-containing medium and incubating the complex-containing medium to yield a product-containing reaction medium comprising compounds comprising a thiol and at least one metabolite compound and isolating a product from the product-containing reaction medium which comprises the compounds to obtain a flavorant product.

20. A process according to claim 19 wherein the yeast is *Saccharomyces cerevisiae*.

21. A process according to claim 1 or 2 wherein the complex-containing medium is incubated under anaerobic conditions.

22. A process according to claim 19 or 20 wherein the complex-containing medium is incubated under anaerobic conditions.

* * * * *